United States Patent [19]

Upchurch et al.

[11] Patent Number: 5,736,036

[45] Date of Patent: Apr. 7, 1998

[54] COLUMN FOR LIQUID CHROMATOGRAPHY

[75] Inventors: Paul E. Upchurch, Coupeville; Hans G. Schick, Anacortes, both of Wash.

[73] Assignee: Upchurch Scientific, Inc., Oak Harbor, Wash.

[21] Appl. No.: 381,294

[22] Filed: Jan. 31, 1995

Related U.S. Application Data

[63] Continuation of Ser. No. 62,402, May 14, 1993, abandoned.

[51] Int. Cl.$^6$ ............................................. B01D 15/08
[52] U.S. Cl. ................................. 210/198.2; 210/656
[58] Field of Search ........................... 210/635, 656, 210/198.2, 541, 232, 238; 96/101, 104, 106

[56] References Cited

U.S. PATENT DOCUMENTS

| | | | |
|---|---|---|---|
| 3,583,230 | 6/1971 | Patterson | 210/198.2 |
| 3,682,315 | 8/1972 | Haller | 210/198.2 |
| 3,763,879 | 10/1973 | Jaworek | 210/198.2 |
| 3,855,130 | 12/1974 | Randau | 210/198.2 |
| 3,878,099 | 4/1975 | Ogle | 210/198.2 |
| 3,904,527 | 9/1975 | Wilhelmson | 210/198.2 |
| 3,926,800 | 12/1975 | Stephens | 210/198.2 |
| 4,093,550 | 6/1978 | Stahl | 210/198.2 |
| 4,187,177 | 2/1980 | Stahl | 210/198.2 |
| 4,283,280 | 8/1981 | Brownlee | 210/198.2 |
| 4,293,415 | 10/1981 | Bente | 210/198.2 |
| 4,313,828 | 2/1982 | Brownlee | 210/198.2 |
| 4,389,313 | 6/1983 | Charney | 210/198.2 |
| 4,451,364 | 5/1984 | Higgins | 210/198.2 |
| 4,522,715 | 6/1985 | Walters | 210/198.2 |
| 4,563,275 | 1/1986 | McEachern | 210/198.2 |
| 4,565,631 | 1/1986 | Hatch | 210/198.2 |
| 4,587,014 | 5/1986 | America | 210/198.2 |
| 4,737,284 | 4/1988 | Hauke | 210/198.2 |
| 4,755,293 | 7/1988 | Sakamoto | 210/198.2 |
| 4,758,340 | 7/1988 | Marchand | 210/450 |
| 4,769,141 | 9/1988 | Couillard | 210/198.2 |
| 4,784,772 | 11/1988 | Gotoh | 210/638 |
| 4,861,473 | 8/1989 | Shackelford | 210/198.2 |
| 4,876,005 | 10/1989 | America | 210/198.2 |
| 4,968,421 | 11/1990 | Spacek | 210/198.2 |
| 5,131,818 | 7/1992 | Wittkop | 417/273 |
| 5,169,522 | 12/1992 | Shalon | 210/198.2 |
| 5,194,225 | 3/1993 | Muller | 210/198.2 |
| 5,238,556 | 8/1993 | Shirkhan | 210/656 |

OTHER PUBLICATIONS

The American College Dictionary Random House, 1970, p. 458.
Upchurch, HPLC Fittings, 2d ed. 1992, pp. 1–47.
*1992 Upchurch Scientific* catalog, p. 89, published by Upchurch Scientific in the U.S.A. Feb. 1992.
*1991 Alltech* catalog, p. 602, published by Alltech in the U.S.A. (Undated).
*1993 Alltech* catalog, pp. 431 & 624–625, published by Alltech in the U.S.A. Dec. 1993.
*1992–1993 Keystone* catalog, pp. 66–67, published by Keystone Scientific, Inc., in the U.S.A. Dec. 1991.
*1990 Victrex Peek* brochure, p. 46, published by ICI in the U.S.A., Undated.
*Phase Sep* catalog, p. H–22, published by Phase Separations, Inc. in the U.S.A., Undated.
L. R. Synder and J. J. Kirkland book *Introduction to Modern Liquid Chromatography* (2d ed. 1979), pp. 15–82 & 125–245.

*Primary Examiner*—Ernest G. Therkorn
*Attorney, Agent, or Firm*—Vinson & Elkins L.L.P.

[57] ABSTRACT

A biocompatible column for use in high pressure liquid chromatography applications includes a biocompatible, polymeric inner tube which is located within a metallic outer tube. The polymeric inner tube has end fittings and the inner polymeric tube and such end fittings and comprise a unitary piece. Alternatively, the outside ends of the outer tube may be threaded so that appropriate polymeric end fittings can be removably attached to each end of the column. A liquid chromatography system in which the column of the present invention is used is also shown and described.

20 Claims, 3 Drawing Sheets

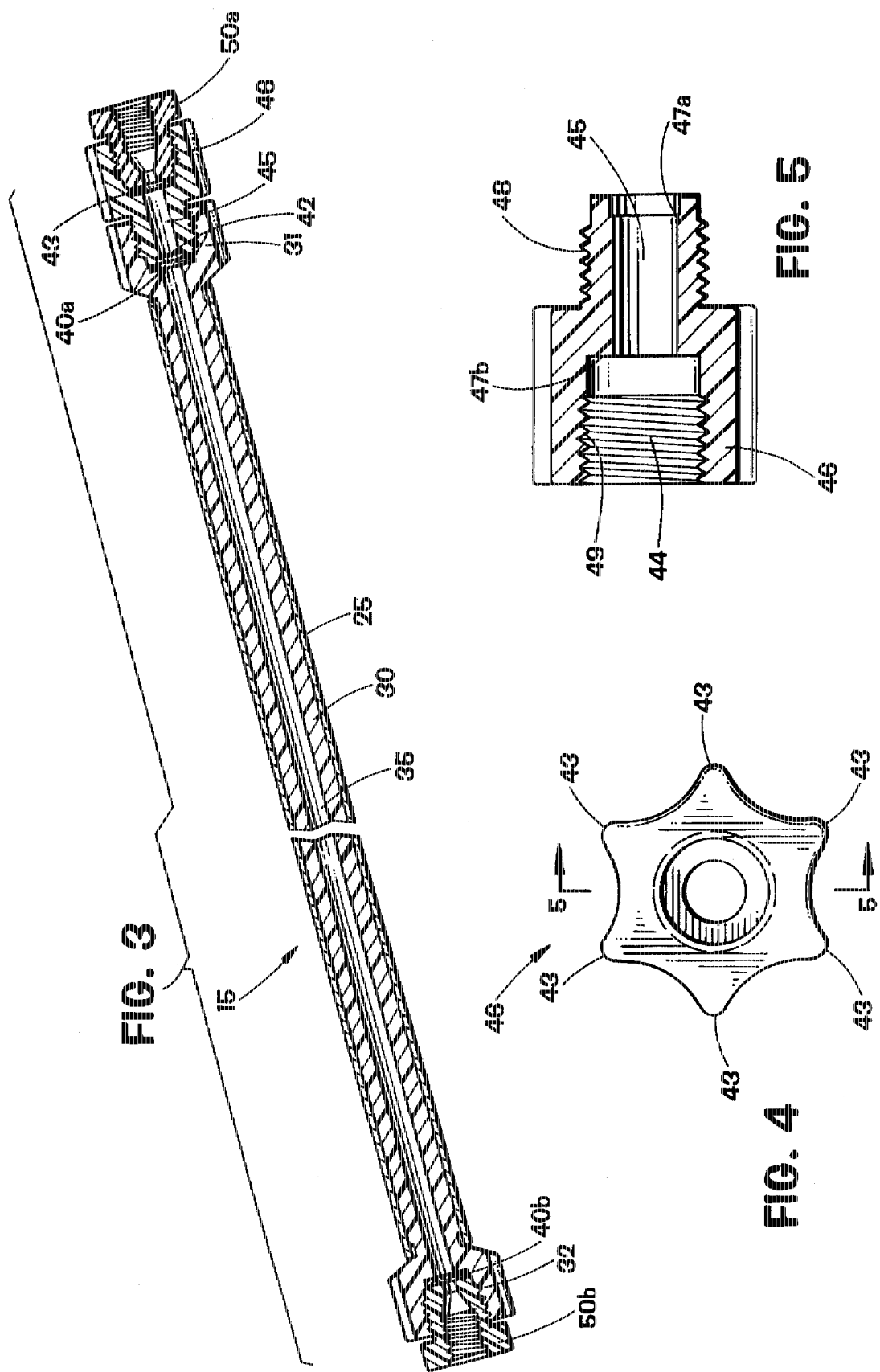

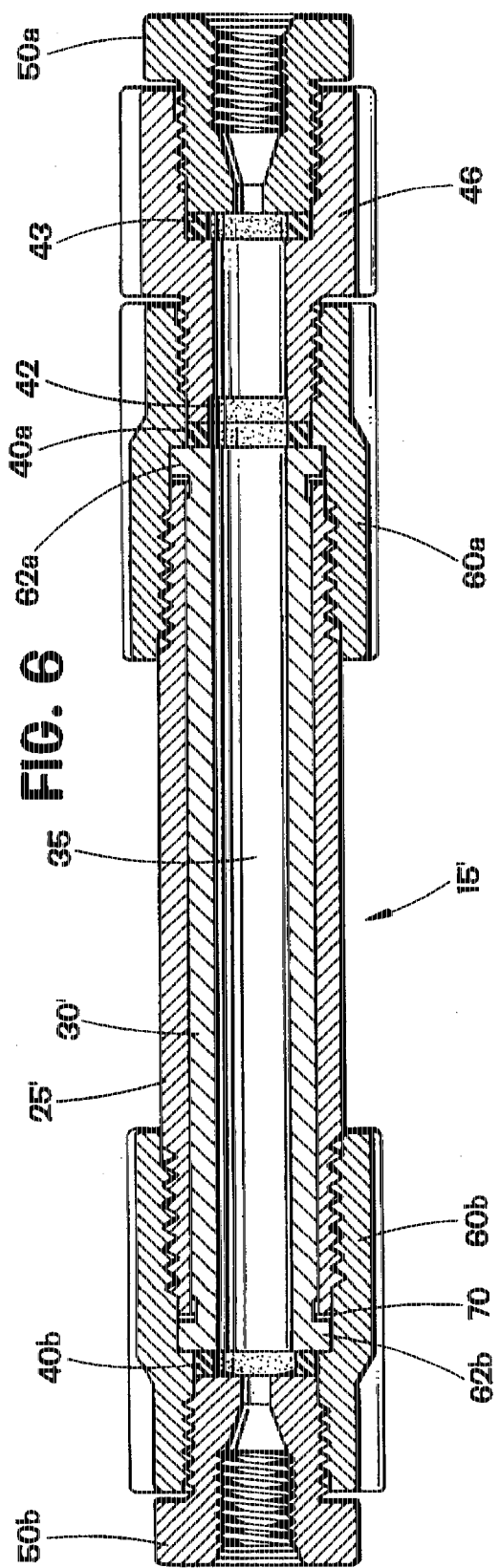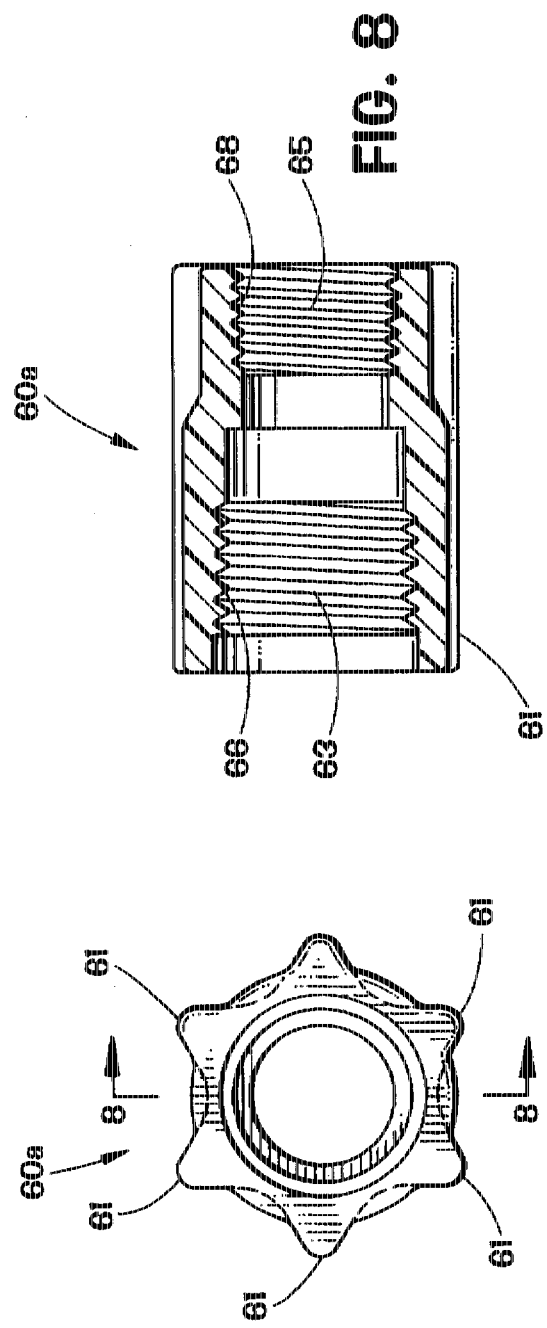

COLUMN FOR LIQUID CHROMATOGRAPHY

This application is a continuation of application Ser. No. 08/062,402, filed May 14, 1993, and entitled "Column for Liquid Chromatography," now abandoned.

FIELD OF THE INVENTION

This invention relates generally to an improved column for use in liquid chromatography applications, and relates more particularly to a column well-suited for applications involving relatively high pressures and/or requiring biocompatibility.

BACKGROUND OF THE INVENTION

Liquid chromatography (LC) is a well-known technique for separating the constituent elements in a given sample. In a conventional LC system, a liquid solvent (referred to as the "mobile phase") is introduced from a reservoir and is pumped through the LC system. The mobile phase exits the pump under pressure. The mobile phase then travels via tubing to a sample injection valve. As the name suggests, the sample injection valve allows an operator to inject a sample into the LC system, where the sample will be carried along with the mobile phase.

The next most significant element in the LC system is the column. A typical column usually consists of a piece of steel tubing which has been packed with a "packing" material. The "packing" consists of the particulate material "packed" inside the column. It usually consists of silica- or polymer-based particles, which are often chemically bonded with a chemical functionality. When the sample is carried through the column (along with the mobile phase), the various components (solutes) in the sample migrate through the packing within the column at different rates (i.e., there is differential migration of the solutes). In other words, the various components in a sample will move through the column at different rates. Because of the different rates of movement, the components gradually separate as they move through the column. Differential migration is affected by factors such as the composition of the mobile phase, the composition of the stationary phase (i.e., the material with which the column is "packed"), and the temperature at which the separation takes place. Thus, such factors will influence the separation of the sample's various components. A more detailed description of the separation process can be found, among other places, in Chapters 2 and 5 of *Introduction to Modern Liquid Chromatography* (2d ed. 1979) by L. R. Snyder and J. J. Kirkland, which chapters are incorporated by reference herein.

Once the sample (with its components now separated) leaves the column, it flows with the mobile phase past a detector. The detector detects the presence of specific molecules or compounds. As discussed in Chapter 4 of *Introduction to Modern Liquid Chromatography*, which chapter is incorporated by reference herein, two general types of detectors are used in LC applications. One type measures a change in some overall physical property of the mobile phase and the sample (such as their refractive index). The other type measures only some property of the sample (such as the absorption of ultraviolet radiation). In essence, a typical detector in an LC system can measure and provide an output in terms of mass per unit of volume (such as grams per milliliter) or mass per unit of time (such as grams per second) of the sample's components. From such an output signal, a "chromatogram" can be provided; the chromatogram can then be used by an operator to determine the chemical components present in the sample.

In addition to the above components, an LC system will often include filters, check valves, or the like in order to prevent contamination of the sample or damage to the LC system. It will be understood to those skilled in the art that, as used herein, the term "LC system" is intended in its broad sense to include all apparatus used in connection with liquid chromatography, whether made of only a few simple components or made of numerous, sophisticated components which are computer controlled or the like.

Many different types of LC systems and components for LC systems are commercially available from a number of vendors. For example, Millipore Corporation of Milford, Mass., Beckman Instruments of Fullerton, Calif., and Hewlett-Packard Co. of Palo Alto, Calif., all sell LC systems, including pumps, sample injection valves, columns, and detectors, among other things. In addition, various columns with various packings are commercially available from a variety of sources, including (among others) Baxter Healthcare Corporation of Deerfield, Ill., Supelco of Bellafonte, Penn., and Alltech Associates, Inc., also of Deerfield, Ill.

Today, most LC systems include pumps which can generate relatively high pressures of up to around 6,000 psi. In many situations, an operator can obtain successful results by operating an LC system at "low" pressures of anywhere from just a few psi or so up to 1,000 psi or so. More often than not, however, an operator will find it desirable to operate an LC system at relatively "higher" pressures of over 1,000 psi. The operation and use of LC systems at such "higher" pressure levels is often referred to as "high pressure liquid chromatography" or "high performance liquid chromatography" (HPLC).

In order to be suitable for HPLC applications, a column must be made to withstand the typical operating pressures of the LC system. If the column is too weak, it may burst and thereby leak. Given the types of solvents that are sometimes used as the mobile phase and the expense of obtaining and/or preparing many samples for use, any such failure of a column is a serious concern. Even though the required pressures for many HPLC applications may be only several thousand psi or so during operation, the "packing" of a column, however, may involve pressures of about 10,000 to 15,000 psi. Besides being able to withstand such pressures, the column must be made of a material which can withstand the chemical action of the mobile phase; i.e., the ideal column is chemically inert to the mobile phase used. In addition, the column needs to be durable so that it has a commercially useful life span.

Given such concerns, conventional columns typically consist of a stainless steel tube which had stainless steel end fittings attached at each end. Often, such columns were "packed" with appropriate materials to achieve the chemical separation required of the column. A detailed discussion of end fittings, and column end fittings in particular, can be found in Chapter VII of the booklet *HPLC Fittings* (2d ed. 1992) by Paul Upchurch, which chapter is incorporated by reference herein. Typical column end fittings must hold to operating pressures of up to 6,000 psi or so. Because such columns are typically "packed" at pressures of up to 10,000 to 15,000 psi or so, such end fittings must be able to withstand such higher pressures as well. Hence, such column end fittings usually have been machined from stainless steel. The end fittings also must be suitable for connecting the column to the tubing used in the LC system to connect the various elements of the LC system with one another.

The inside diameter of the column must be polished in order to eliminate the possible adverse effects a rough inside wall may have on the separation process. It has been suggested that the smoothness of the inside wall of the column influences the homogeneity of the packing. Hence, a smoother surface finish on the column's inside surface results in a better level of performance from the column. Accordingly, most conventional columns typically consist of a stainless steel column with a highly polished inside diameter surface finish. Although such a polished finish is important, it requires additional manufacturing steps and can be expensive to obtain.

More recently, it has been realized that the use of stainless steel columns (as well as stainless steel tubing and other steel components in an LC system) have potential drawbacks in situations involving biological samples. For example, the components in a sample may attach themselves to the wall of a stainless steel column. This presents problems because the detector's measurements (and thus the chromatogram) of a given sample may not accurately reflect the sample if some of the sample's ions remain in the column and do not pass the detector. Perhaps of even greater concern, however, is the fact that ions from the stainless steel column may detach from the column and flow past the detector, thus leading to potentially erroneous results. Hence, there is a need for a "biocompatible" column; i.e., a column made of a material which is chemically inert with respect to such "biological" samples and the mobile phase used with such samples so that ions will not be released by the column and thus contaminate the sample.

To avoid such biocompatibility problems, glass lined columns which have an exterior made of stainless steel are known. Because such columns are prone to breakage, a great deal of care in the manufacture, transportation, handling, and use of such columns is required. Moreover, it has been observed that the use of such glass-lined columns at high pressures is not appropriate. Columns using extruded rods or tubing made of the polymer polyetheretherketone (PEEK) with molded or machined PEEK column end fittings are also known, but because of their lack of strength, such columns are typically limited to applications using fairly low pressures (i.e., pressures of not more than 200 psi or so), although some columns with larger walls have been claimed to work at up to 2,000 psi or so. Columns made of the polymer PEEK are also known, but such columns are machined from large diameter PEEK rods. In order to produce such PEEK columns in this way, the PEEK tube must first be machined and then its inside diameter must be polished. This approach thus involves additional manufacturing steps which add additional costs. Also, the surface finish obtained in such columns, while acceptable for many LC applications, is often unacceptable for applications where high levels of performance are required of the column. Moreover, to hold to the high pressures at which many columns are packed and at which some LC systems operate, such PEEK columns must be made with a very thick wall.

Another conventional column includes a PEEK rod surrounded by an aluminum jacket. However, the use of PEEK rods still requires the extra manufacturing costs and therefore added time and expense. In addition, the surface finish obtained via such an approach may not be acceptable for LC applications requiring high performance by the column. Such columns also require the use of specialized, metallic end fittings which can handle the higher pressures but which require the use of additional polymeric pieces to ensure biocompatibility. The use of such additional pieces results in a higher chance that a connection between some of the pieces will leak or fail, an obviously undesirable result. Such additional pieces and joints also may decrease the durability of such columns.

Therefore, it is an object of the present invention to provide a biocompatible column which can be used in relatively high pressure LC applications and which has sufficient strength for use in relatively high pressure LC applications.

It is yet another object of the present invention to provide a biocompatible column which is not fragile and which does not require excessive manufacturing steps or costs.

It is still another object of the present invention to provide a biocompatible column with a highly polished inside surface and with a minimal number of pieces.

It is still another object of the present invention to provide a durable, biocompatible column which can provide a high level of performance at relatively high pressures with a minimal chance of leakage.

The above and other advantages of the present invention will become readily apparent to those skilled in the art from the following detailed description of the present invention, and from the attached drawings, which are briefly described below.

SUMMARY OF THE INVENTION

The present invention may be implemented as a metal tube to provide an outer column jacket, within which the body of a biocompatible, polymeric tube is located. The polymeric inner tube is molded in place relative to the outer tube so that it forms column end fittings extending beyond the two open ends of the outer tube of the column. Hence, the inner tube and the two end fittings are unitary. The two end fittings have an outside diameter greater than the inside diameter of the metal tube, thus preventing the separation of the inner tube from the outer tube. Such an arrangement proves advantageous because the outer metal tube provides sufficient strength to allow the column to operate at relatively high pressures. At the same time, however, the polymeric inner tube and end fittings provide only chemically inert surfaces and thus provide biocompatibility. As a whole, such a column can operate at the relatively higher pressures associated with metal columns, yet provide the biocompatibility associated with polymeric materials. In an alternative embodiment of the present invention, the inner tube may have shoulders which extend beyond the open ends of the outer tube, with biocompatible couplings removably attached to threads provided on the outer surface of the metal tube.

BRIEF DESCRIPTION OF THE DRAWINGS

FIG. 3 is a cross-sectional view of a column in accordance with the present invention to which frits, a guard column, and fittings have been attached.

FIG. 4 is an end view of a guard column for use with a column in accordance with the present invention.

FIG. 5 is a cross-sectional view taken along line 5—5 of the guard column.

FIG. 6 is a cross-sectional view of an alternative embodiment of the column in accordance with the present invention.

FIG. 7 is an end view of a coupling used in connection with the column in accordance with an alternative embodiment present invention.

FIG. 8 is a cross-sectional view taken along line 8—8 of the coupling.

DETAILED DESCRIPTION OF THE INVENTION

Figure 1:
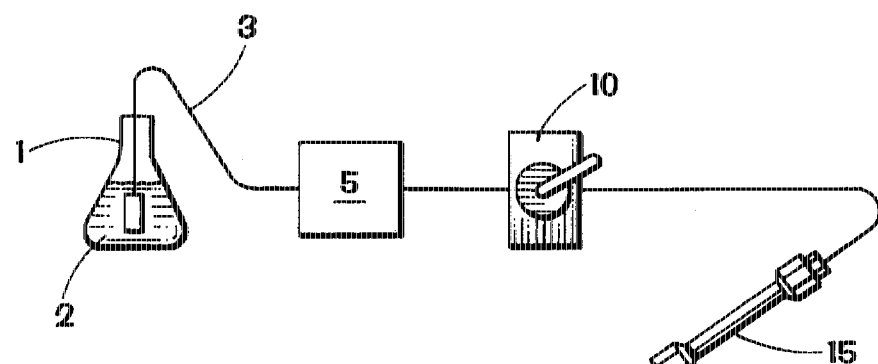
FIG. 1 is a block diagram of a LC system.
Figure 1:
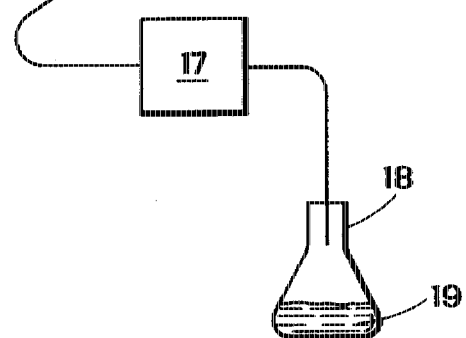

In FIG. 1, a block diagram of the essential elements of an LC system which includes a column 15 in accordance with the present invention is provided. A reservoir 1 contains a solvent or mobile phase 2. Tubing 3 connects the mobile phase 2 in the reservoir 1 to a pump 5. The pump 5 is connected to a sample injection valve 10 which, in turn, is connected via tubing to a first end of a column 15. The second end of the column 15 is then connected via tubing to a detector 17. After passing through the detector 17, the mobile phase 2 and the sample injected via injection valve 10 are expended into a second reservoir 18, which contains the chemical waste 19. As noted above, the sample injection valve 10 is used to inject a sample of a material to be studied into the LC system. The mobile phase 2 flows through the tubing 3 which is used to connect the various elements of the LC system together.

When the sample is injected via sample injection valve 10 in the LC system, the sample is carried by the mobile phase through the tubing into the column 15. As is well known in the art, the column 15 contains a packing material which acts to separate the constituent elements of the sample. After exiting the column 15, the sample (as separated via the column 15) then is carried to and enters a detector 17, which detects the presence or absence of various chemicals. The information obtained by the detector 17 can then be stored and used by an operator of the LC system to determine the constituent elements of the sample injected into the LC system.

Figure 2:
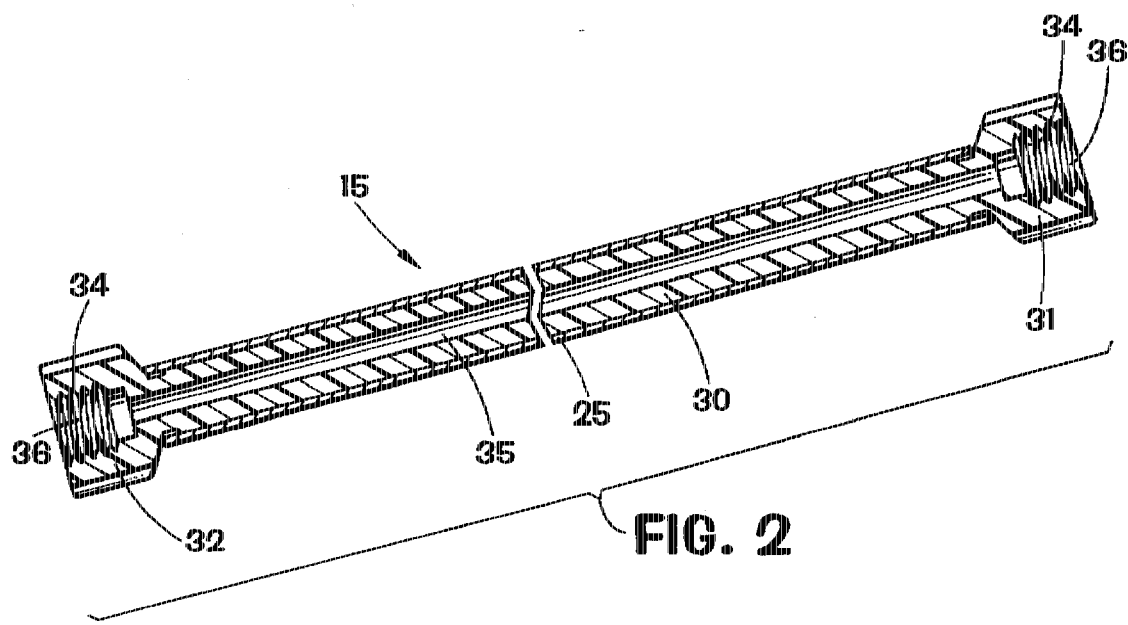
FIG. 2 is a cross-sectional view of a column in accordance with the present invention.

Referring now to FIG. 2, a cross-sectional view of a column 15 in accordance with the present invention is shown. The column 15 consists of an outer tube 25 surrounding an inner tube 30. As shown in FIG. 2, the inner tube 30 has a passageway 35 extending along the longitudinally axis therethrough. Column 15 also includes end fittings 31 and 32 at its first and second ends. As seen in FIG. 2, the end fittings 31 and 32, together with the inner tube 30, comprise a unitary piece. The end fittings 31 and 32 extend beyond the first and second ends of the outer tube 25, respectively. Because the outer diameter of at least a portion of each of the end fittings 31 and 32 exceeds the inside diameter of the outer tube 25, the unitary piece comprising the inner tube 30 and the end fittings 31 and 32 cannot be pulled through and hence separated from the outer tube 25. In short, the end fittings 31 and 32 prevent the inner tube 30 and the outer tube 25 from longitudinally moving more than a short distance relative to one another. Each of the end fittings 31 and 32 has a threaded counterbore 36. The threads 34 in the threaded counterbores 36 are provided in order to allow fittings and/or a guard column (shown in FIG. 3) to be removably attached to the column 15.

The outer tube 25 can be made of almost any metal. For best results, we prefer to use a seamless anodized aluminum tube, although steel, copper, brass and other metals may be used. The metallic outer tube 25 provides support and strength to the column 15, thereby ensuring that the column 15 can be used in high pressure liquid chromatography applications and can be packed with a packing material at pressures of up to 10,000 to 15,000 psi. In operation, the passageway 35 of the column 15 is filled with any one of a number of packing materials (not shown). It will be apparent to those skilled in the art how the passageway 35 can be packed with appropriate packing materials. By ensuring that the passageway 35 through the column 15 can be packed at pressures of up to 10,000 to 15,000 psi or so, it can be seen that the column 15 can be used in operation in an LC system at relatively high operating pressures of 3,000 to 5,000 psi or so.

At the first and second ends of the column 15 are column end fittings 31 and 32, respectively. As shown in FIG. 2, column end fittings 31 and 32 are contiguous with the inner tube 30. We prefer to have the column end fittings 31 and 32, together with the inner tube 30, comprise a single polymeric piece. This can be accomplished through an appropriate manufacturing process in which the inner tube 30 and the column end fittings 31 and 32 are molded in place within the outer tube 25, thereby forming a unitary polymeric piece which provides a column 15 which has an outer tube 25, an inner tube 30, and also column end fittings 31 and 32. The unitary inner tube 30 and end fittings 31 and 32 provide the advantage of using less pieces than conventional columns, thus resulting in less joints and therefore less chance of having the pieces separate (which could result in leakage or additional dead volumes) or of leakage. In addition, this approach eliminates the manufacturing steps involving the assembly of the various pieces. It also allows us to obtain a smoother surface finish on the inside surface of the inner tube 30 at a lower cost than is obtained via conventional machining of rods made of the polymer PEEK. For example, the inside surface of the inner tube 30 of the column 15 of the present invention can easily have a surface finish with a root mean square (rms) value of about 8 micro-inches or better, as opposed to conventional columns which have a surface finish of about 32 micro-inches only after extensive machining operations.

As shown in FIG. 2, located within the outer tube 25 and adjacent to and in contact with the surface of the inside diameter of outer tube 25 is the outside diameter of the inner tube 30. Preferably, the inner tube 30 is made of the synthetic polymer polyetheretherketone, which is commercially available under the trademark "PEEK" from ICI Americas.

The polymer PEEK has the advantage of providing a high degree of chemical inertness and therefore biocompatibility; it is chemically inert to most of the common solvents used in LC applications, such as acetone, acetonitrile, and methanol (to name a few). At the same time, an inner tube 30 made of PEEK which is "reinforced" by a metallic outer tube 25 is capable of withstanding the high pressures of 10,000 to 15,000 psi at which the column 15 is to be packed. PEEK also can be machined by standard machining techniques to provide smooth threads 34 or the like. As noted above, the inside surface of the inner tube 30 must be highly polished so as to reduce the potential adverse consequences of having a rough inside surface of column 15. Generally, a very smooth surface of the inside diameter of inner tube 30 can be obtained via the molding process used to form the inner tube 30. Molding the inner tube 30 makes it easier and cheaper to obtain a smoother surface. This approach also eliminates the steps of drilling through a PEEK rod and then polishing the inner surface of the hole drilled.

For best results, we prefer to use an inner tube 30 which is made primarily of the polymer PEEK and which is 5% by weight filled with glass, fiberglass, or carbon strands or fibers. Additional or lesser amounts of glass or fiberglass fillers could be used with PEEK to make the inner tube 30. Although we prefer to use the polymer PEEK for best results, it will be obvious to those skilled in the art that other chemically inert synthetic polymerics, such as polytetrafluoroethylene (which is sold by DuPont under the trademark "TEFLON") or chlorotetrafluoroethylene (which is sold by 3M under the trademark "KEL-F") or the polymer sold under the trademark VESPEL, can be used to form the inner tube 30.

Although the polymer PEEK is substantially chemically inert with respect to most solvents used as the mobile base for LC applications, there are a few solvents which may cause PEEK to swell. Such solvents include dimethylsulfoxide, methylene chloride, and tetrahydrofuran. In addition to its other advantages, the use of the metallic outer tube 25 helps prevent and control the swelling which may be caused by the use of such solvents.

In situations where only relatively lower pressures are likely to be used, a column 15 with an inner tube 30 made of the synthetic polymer sold under the trademark TEFZEL may be more appropriate. For example, if an operator wants to use concentrated nitric acid or sulfuric acid as the mobile phase, a column 15 with an inner tube 30 made of PEEK is not appropriate due to the reaction of PEEK to concentrated nitric acid and sulfuric acid.

With reference to FIG. 2, it can be seen that the outer surface of the inner tube 30 is adjacent to and contacts the inner surface of the metallic outer tube 25. In the preferred embodiment, the outer surface of the inner tube 30 is molded so that it is attached to the inner surface of the outer tube 25. In the molding process, the inner surface of the outer tube 25 serves as part of the mold which shapes the inner tube 30. Attaching the inner surface of the outer tube 25 and the outer surface of the inner tube 30 prevents the inner tube 30 and outer tube 25 from moving either radially or longitudinally relative to one another. Of course, the outer surface of the inner tube 30 need not be attached to the inner surface of the outer tube 25. The end fittings 31 and 32 which extend beyond the open ends of the outer tube 25 prevent anything more than a relatively modest amount of longitudinal movement between inner tube 30 and outer tube 25 relative to one another. Hence, the end fittings 31 and 32 secure the body of the inner tube 30 within the outer tube 25 and prevent the outer tube 25 from being removed from the inner tube 30.

Now referring to FIG. 3, the column 15 is shown in a cross-sectional view as assembled with frits 40a and 40b, a guard column assembly 46 (which includes frits 42 and 43) and fittings 50a and 50b. Porous disks (or frits) 40a, 40b, 42, and 43, respectively are used for filtering the mobile phase and the sample as they move through an LC system. The frits 40a, 40b, 42, and 43 can be of a type which is commonly known and commercially available from Upchurch Scientific, Inc., of Oak Harbor, Wash. Frits 40a, 40b, 42, and 43 may be made of materials such as titanium or sintered PEEK. For best results, we prefer to use biocompatible frits 40a, 40b, 42, and 43 made of the polymer ultra-high molecular weight polyethylene.

As shown in FIG. 3, a guard column 46 is removably screwed into the threaded counterbore of end fitting 31. Many LC systems include a guard column to "guard" the main column from the introduction of unwanted sample components that might irreversibly bind to the packing in the main column. Preferably, the guard column 46 has a relatively small volume in its passageway 45 (as compared to the volume of the passageway 35 of the column 15) and is easy to remove from the LC system and/or replace. In FIG. 3, the guard column 46 has a frit 42 located therein. The frit 42 is preferably located so that, when the guard column 46 is securely attached to the column 15, one of the circular faces of the frit 42 is adjacent to the frit 40a.

The guard column 46 (and the frit 42) can be of any type of those which are commercially available, such as those which are available from Upchurch Scientific, Inc., of Oak Harbor, Wash. (The guard column 46 is discussed in more detail below.) Similarly, the fittings 50a and 50b can be of a type commonly known, such as those which are available from Upchurch Scientific, Inc. As shown in FIG. 3, the fittings 50a and 50b have been attached to the guard column 46 and the end fitting 32, respectively, by screwing the fittings 50a and 50b into the threaded counterbores of the guard column 46 and the end fitting 32, respectively.

Now referring to FIGS. 4 and 5, the guard column 46 is shown in additional detail. The guard column 46 has several fins 43, which extend outwardly from the center of the guard column 46. The fins 43 allow an operator to easily grip and turn the guard column 46, thus allowing the operator to either screw or unscrew the guard column 46 into or out of the threaded counterbore 36 of the end fitting 31 (the guard column 46 is shown as secured in the end fitting 31 in FIG. 3).

In FIG. 5, it can be seen that the guard column 46 has at one end a threaded counterbore 44. The counterbore 44 is designed and threaded so that a threaded fitting 50a can be removably secured therein (as is shown in FIG. 3). As is well known in the art, the fitting 50a can be used to secure one end of a hollow tube (not shown) to the column assembly. The threaded counterbore 44 is in fluid communication with a passageway 45, which extends from the "bottom" of the threaded counterbore 44 through the rest of the body of the guard column 46 up to the seat 47a. The seat 47a is designed to snugly fit and hold the frit 42 (discussed below). In operation, the passageway 45 of the guard column 46 is filled with an appropriate packing material (not shown). It will be apparent to those skilled in the art how the passageway 45 can be packed with an appropriate packing material.

Still referring to FIG. 5, the guard column 46 has a threaded end 48. The threaded end 48 is designed and threaded so that it can be removably secured to the threaded counterbore 34 of either of the end fittings 31 or 32 of the column 15. The threaded end 48 can be screwed into the counterbore 34 to secure the guard column 46 to the end fitting 31 or can be unscrewed from the counterbore 34 to detach the guard column 46 from the end fitting 31.

For best results, we prefer to use a biocompatible guard column 46 which is made of a mixture of the polymer polyetheretherketone ("PEEK") and is about 30% by weight filled with glass or fiberglass strands or fibers. Of course, greater or lesser amounts of glass, fiberglass, or carbon could be used to make the body of guard column 46. Similarly, materials other than glass or fiberglass could be used. As noted above, a suitable biocompatible guard column 46 can be obtained from Upchurch Scientific, Inc., of Oak Harbor, Wash.

At the second end of the guard column 46 is a seat 47a, as shown in FIG. 5. The seat 47a is designed so that it will hold the frit 42 in place when the guard column 46 is secured to the end fitting 31 (as is shown in FIG. 3). For best results, we prefer to use a biocompatible guard column 46, including a biocompatible frit 42, such as those which are commercially available from Upchurch Scientific, Inc.

Now referring to FIG. 6, an alternative embodiment of the invention is shown. In FIG. 6, the column 15' has an inner tube 30'. The inner tube 30' has shoulders 62a and 62b which extend beyond the first and second ends, respectively, of the outer tube 25'. For best results, we prefer that the outside diameter of the shoulders 62a and 62b be no greater than the minimum outside diameter of the outer tube 25', which exists at the very ends of the outer tube 25' (i.e., beyond the threads at each end). As shown in FIG. 6, this size is preferred because it allows the couplings 60a and 60b to be attached to the column 15' around the shoulders 62a and 62b. At the same time, however, the shoulders 62a and 62b have an outside diameter greater than the inside diameter of the outer tube 25'. Hence, the shoulders 62a and 62b secure the body of the inner tube 30' within the outer tube 25' by preventing more than a modest amount of longitudinal movement by the inner tube 30' relative to the outer tube 25'. An L-shaped gap 70 exists between the shoulders 62a and 62b and the first and second ends of the outer tube 25'. These gaps 70 are provided because the polymeric material used to form the inner tube 30' shrinks as it cools. Hence, the gaps 70 are left from the molding process used to mold the inner tube 30'.

Still referring to FIG. 6, the outside surface of the inner tube 30' is adjacent to and contacts the inside surface of the outer tube 25'. The inner tube 30' need not be attached to the outer tube 25'. Instead, the outer surface of the inner tube 30' between the shoulders 62a and 62b may be located within and not attached to the inside surface of the outer tube 25'. As noted above, the shoulders 62a and 62b secure the body of the inner tube 30' within the outer tube 25'. We prefer to use an outer tube 25' made of anodized aluminum, together with an inner tube 30' made of the polymer PEEK. The inner tube 30' has a passageway 35 which extends therethrough. As discussed above, the passageway 35 provides an appropriate location for the packing material (not shown).

Referring now to FIGS. 7 and 8, the coupling 60a is shown. Preferably, couplings 60a and 60b are essentially the same and are freely interchangeable with one another. Hence, the following discussion of coupling 60a generally applies to coupling 60b as well. An end view of the coupling 60a is provided in FIG. 7. Fins 61 extend around the outer surface of the coupling 60a. These make it easier for the operator to grip and turn the coupling 60a, thereby allowing an operator to easily screw the coupling 60a onto the column 15' (as shown in FIG. 6) or to unscrew and detach the coupling 60a from the column 15'.

In FIG. 8, first and second threaded counterbores 63 and 65, respectively, are shown. The first counterbore 63 is designed and threaded so that it mates with one of the threaded ends of the column 15' (as shown in FIG. 6). This allows the coupling 60a to be removably secured to the column 15' by screwing them together (as shown in FIG. 6). The second threaded counterbore 65 is designed and threaded so that it can mate with the threaded end of either a fitting 50b (as shown in FIG. 6 for coupling 60b) or a guard column 46 (as shown in FIG. 6 for coupling 60a).

For best results, we prefer to use a biocompatible coupling 60a which is made of a mixture of the synthetic polymer PEEK and is about 30% by weight filled with carbon fibers. Of course, greater or lesser amounts of carbon fibers may be used and, instead of carbon fibers, other fillers such as glass or fiberglass strands or fibers may be used. Such a biocompatible coupling 60a thus ensures that the coupling 60a, as well as the column 15', will present only chemically inert surfaces which can come into contact with the mobile phase and sample.

EXAMPLE

The following describes only one possible specific embodiment of my invention, and is not to be considered as limiting the scope of the claims. Referring back to FIG. 3, an appropriate column 15 can be described as follows: The length of the column 15 (i.e., the length of the packed bed which is located in the passageway 35) is 15 cm (not including end fittings 31 and 32). The diameter of the passageway 35 in the column 15' is 2 mm. The outer tube 25 is made of anodized aluminum and the inner tube 30 is made of the polymer PEEK, which is commercially available from ICI Americas. In addition, the column 15 is packed with one of a variety of well-known packing materials, such as any one of the following: C-18, C-8, or silicon.

While the present invention has been shown and described in its preferred embodiment and in certain specific alternative embodiments, those skilled in the art will recognize from the foregoing discussion that various changes, modifications, and variations may be made thereto without departing from the spirit and scope of the invention as set forth in the claims. Hence, the embodiments and specific forms, materials, and the like are merely illustrative and do not limit the scope of the invention or the claims herein.

We claim the following:

1. A liquid chromatography column which comprises:
   an outer metal tube having first and second ends; and
   a biocompatible inner tube having a passageway therethrough and having first and second ends, wherein at least a portion of said inner tube is located within said outer metal tube and wherein portions of the first and second ends of said inner tube form shoulders which extend beyond the first and second ends, respectively, of said outer tube, and wherein the shoulders and said inner tube comprise a unitary piece and the shoulders each have an outside diameter greater than the inside diameter of said metal tube, preventing separation of said inner tube from said outer tube.

2. The liquid chromatography column according to claim 1 wherein the portions of said inner tube extending beyond the first and second ends of said outer tube comprise first and second end fittings.

3. The liquid chromatography column according to claim 2 further comprising a biocompatible guard column removably secured to one of said end fittings.

4. The liquid chromatography column according to claim 1 wherein the portions of said inner tube extending beyond the first and second ends of said outer tube further comprise:
   a first biocompatible end fitting which extends beyond the first end of said outer tube; and
   a second biocompatible end fitting which extends beyond the second end of said outer tube, wherein said first and second end fittings and said inner tube comprise a unitary piece.

5. The liquid chromatography column according to claim 1 further comprising:
   a first biocompatible coupling member; and
   a second biocompatible coupling member, wherein the first end of said outer tube is removably secured to said first coupling member and wherein the second end of said outer column is removably secured to said second coupling member.

6. The liquid chromatography column according to claim 1 wherein at least a portion of the outside surface of said inner tube is attached to at least a portion of the inside surface of said outer tube.

7. The liquid chromatography column according to claim 1 wherein said inner tube comprises polyetheretherketone.

8. The liquid chromatography column according to claim 7 wherein said inner tube further comprises glass fibers.

9. The liquid chromatography column according to claim 1 wherein said metal outer tube comprises stainless steel.

10. The liquid chromatography column according to claim 1 wherein said metal outer tube comprises aluminum.

11. The liquid chromatography column according to claim 1 further comprising a frit removably held against at least one end of said inner tube.

12. The liquid chromatography column according to claim 1 further comprising a packing material located within the passageway of said inner tube.

13. The liquid chromatography column according to claim 1 wherein said inner tube comprises a polymeric piece molded in place relative to said outer tube.

14. The liquid chromatography column according to claim 1 wherein the passageway of said inner tube has a smooth inner surface.

15. The liquid chromatography column according to claim 14 wherein the inner surface of the passageway has a surface finish with a root mean square value of no greater than about eight microinches.

16. A liquid chromatography column which comprises:

a cylindrical outer metal tube having a first end and a second end;

a cylindrical, biocompatible inner tube having a passageway therethrough, wherein at least a portion of said inner tube is located within said outer tube and wherein said inner tube has unitary first and second end fittings and at least a portion of each of said first and second end fittings has an outside diameter greater than the inside diameter of said outer tube, preventing separation of said inner tube and said outer tube.

17. The liquid chromatography column according to claim 16, wherein each of said first and second end fittings has a counterbore, and further comprising first and second frits located in the counterbores of the first and second end fittings, respectively.

18. The liquid chromatography column according to claim 16, wherein at least a portion of the outside surface of said inner tube is attached to at least a portion of the inside surface of said outer tube.

19. The liquid chromatography column according to claim 16 further comprising a packing material within the passageway of said inner tube.

20. A liquid chromatography column which comprises:

an outer metal tube having first and second ends;

a biocompatible inner tube having a passageway therethrough and having first and second ends, wherein at least a portion of said inner tube is located within said outer tube, and wherein portions of the first and second ends of said inner tube comprise end fittings which are located beyond the first and second ends, respectively, of said outer tube, and wherein at least a portion of each of the end fittings has an outside diameter greater than the inner diameter of said outer tube, thereby preventing the separation of said inner tube and said outer tube, and wherein said inner tube and the first and second end fittings comprise a unitary, molded piece.

* * * * *